(12) United States Patent
Ono et al.

(10) Patent No.: US 6,566,350 B2
(45) Date of Patent: May 20, 2003

(54) MINOCYCLINE-CONTAINING COMPOSITIONS

(75) Inventors: Kazuhiro Ono, Souka (JP); Hidenari Sakaguchi, Kawasaki (JP); Ikuto Hayakawa, Funabashi (JP)

(73) Assignee: Showa Yakuhin Kako Co., Ltd., Tokyo (JP)

( * ) Notice: Subject to any disclaimer, the term of this patent is extended or adjusted under 35 U.S.C. 154(b) by 0 days.

(21) Appl. No.: 09/860,503

(22) Filed: May 21, 2001

(65) Prior Publication Data

US 2002/0002151 A1 Jan. 3, 2002

(30) Foreign Application Priority Data

May 23, 2000 (JP) ........................................ 2000-150937

(51) Int. Cl.[7] .............................. A61K 7/16; A61K 31/65
(52) U.S. Cl. ...................... 514/152; 424/49; 424/900; 424/902
(58) Field of Search ........................................ 514/152

(56) References Cited

U.S. PATENT DOCUMENTS

| | | | | |
|---|---|---|---|---|
| 2,627,938 A | * | 2/1953 | Frohmader et al. | 426/358 |
| 2,628,187 A | * | 2/1953 | Frohmader et al. | 424/358 |
| 4,164,564 A | * | 8/1979 | Chen | 424/83 |
| 4,254,105 A | * | 3/1981 | Fukuda et al. | 514/762 |
| 4,379,755 A | * | 4/1983 | Yamada et al. | 514/73 |
| 4,427,670 A | * | 1/1984 | Ofuchi et al. | 424/241 |
| 4,536,519 A | * | 8/1985 | Suzuki et al. | 514/785 |
| 4,822,601 A | * | 4/1989 | Goode et al. | 514/53 |
| 4,867,970 A | * | 9/1989 | Newsham et al. | 424/81 |
| RE33,093 E | * | 10/1989 | Schiracoi et al. | 424/676 |
| 4,882,359 A | * | 11/1989 | Nakegawa et al. | 514/947 |
| 4,946,832 A | * | 8/1990 | Goode et al. | 514/53 |
| 4,965,262 A | * | 10/1990 | Kametaka et al. | 514/230.2 |
| 4,981,693 A | * | 1/1991 | Higashi et al. | 424/435 |
| 4,981,875 A | * | 1/1991 | Levsner et al. | 514/774 |
| 4,983,385 A | * | 1/1991 | Hasegawa et al. | 424/78 |
| 5,112,816 A | * | 5/1992 | Narui et al. | 514/179 |
| 5,122,519 A | * | 6/1992 | Ritter | 514/152 |
| 5,322,689 A | * | 6/1994 | Hughes et al. | 424/401 |
| 5,580,549 A | * | 12/1996 | Fukuda et al. | 424/62 |
| 5,614,178 A | * | 3/1997 | Bloom et al. | 424/68 |
| 5,631,248 A | * | 5/1997 | Davis et al. | 514/179 |
| 5,641,493 A | * | 6/1997 | Date et al. | 424/401 |
| 5,674,509 A | * | 10/1997 | Date et al. | 424/401 |
| 5,858,408 A | * | 1/1999 | Sotani et al. | 424/489 |
| 5,879,689 A | * | 3/1999 | Date et al. | 424/401 |
| 6,096,325 A | * | 8/2000 | Date et al. | 424/401 |
| H2043 H | * | 8/2002 | Decker et al. | 514/559 |
| 6,444,647 B1 | * | 9/2002 | Robinson et al. | 514/17 |
| 6,492,326 B1 | * | 12/2002 | Robinson et al. | 514/2 |

FOREIGN PATENT DOCUMENTS

| | | | |
|---|---|---|---|
| JP | 1-12728 | | 3/1989 |
| JP | 01083019 | * | 3/1989 |
| JP | 2-34325 | | 8/1990 |
| JP | 04013616 | * | 1/1992 |
| JP | 07089847 | * | 4/1995 |
| JP | 10245329 | * | 9/1998 |
| JP | 11286448 | | 10/1999 |
| WO | 9420144 | * | 9/1994 |

OTHER PUBLICATIONS

Abstract of Registered Trademark 617115 "Plastibase" Medicinal (Squibb) Ointment Base, Dec. 1955.*
Abstract of Tanaka et al Yakuzagaku 57(1): 8–15, 1997.*
Abstract of Sotani et al JP 07089847 (Apr. 1995) U.S. 5858408 Nov. 1999.*
The Journal of the Japanese Society of Periodontology, vol. 29, No. 2, pp. 463–471, 472–843, 1987.
English Language Abstract of JP 1–12728.
English Language Abstract of JP 2–34325.
English Language Abstract of JP 11–286448.
The Journal of the Japanese Society of Periodontology, vol. 29, No. 2, pp. 472–843, 1987 (accompanied by an English language abstract).

* cited by examiner

Primary Examiner—Shep K. Rose
(74) Attorney, Agent, or Firm—Greenblum & Bernstein, P.L.C.

(57) ABSTRACT

An object of the present invention is to provide a stable pharmaceutical composition for topical administration comprising minocycline as an active ingredient. According to the present invention, there is provided a pharmaceutical composition for topical administration comprising minocycline or a physiologically acceptable salt thereof in an oleaginous base.

14 Claims, No Drawings

MINOCYCLINE-CONTAINING COMPOSITIONS

TECHNICAL FIELD OF THE INVENTION

The present invention relates to a pharmaceutical composition which comprises minocycline or a physiologically acceptable salt thereof as an active ingredient, and which is useful in the treatment or prevention of a periodontal disease such as periodontitis.

BACKGROUND ART

Periodontitis (proximate periodontitis) is a chronic non-specific inflammation occurring not only in gingiva but also in other periodontia, which in most cases develops from periodontitis simplex. In this disease, periodontal pocket, tooth loosening, alveolar bone absorption, and drainage from the pocket are observed, and most of them progress indolently. It is known that certain gram negative bacilli within the periodontal sulcus are involved in periodontitis. For example, *Bacteriodes gingivalis* is involved in adult periodontitis, *Actinobacillus actinomycetemcomitans* is involved in juvenile periodontitis, and *Bacteriodes intermedius* is involved in acute necrotizing ulcerative periodontitis (The Journal of the Japanese Society of Periodontology, Vol. 29 No. 2 pp463–471).

It is known that minocycline is effective in the treatment of periodontal diseases. Minocycline is one type of tetracycline antibiotics which exhibits strong antibiotic action against the aforementioned periodontal pathogenic bacteria, and exhibits superior clinical efficacy against periodontitis (The Journal of the Japanese Society of Periodontology, Vol. 29 No. 2 pp472–483). For example, there is proposed a method of directly applying an ointment comprising minocycline hydrochloride (3.0%), hydroxymethylcellulose and glycerine to the periodontal pocket. Further, "Periocline dental ointment" (sold by Sunstar Inc.) is being used clinically as a periodontitis therapeutic agent.

However, since minocycline is an unstable substance, techniques for providing a stable composition comprising minocycline as an active ingredient, have been examined. For example, in Japanese Patent Publication No. 1-12728, there is disclosed a non-aqueous composition for topical administration characterized in that minocycline or a physiologically acceptable salt thereof is formulated in a base of polyhydric alcohol which comprises a magnesium compound. Further, in Japanese Patent Publication No. 2-34325, there is disclosed a composition for treatment of periodontal diseases wherein minocycline or a physiologically acceptable salt thereof is formulated with a magnesium compound, an aqueous polymeric substance, a polyhydric alcohol, an ethyl methacrylate/ethyl methacrylate-trimethyl ammonium chloride copolymer, and a solubilizer. Furthermore, Japanese Patent Application Laid-Open No. 11-286448 discloses a pharmaceutical composition for topical administration comprising minocycline or a physiologically acceptable salt thereof and an aluminium compound in a polyhydric alcohol base.

SUMMARY OF THE INVENTION

An object of the present invention is to provide a stable pharmaceutical composition for topical administration comprising minocycline as an active ingredient. Another object of the present invention is to provide a substance for stabilizing minocycline formulated in a pharmaceutical composition for topical administration.

As a result of focused and deliberate efforts to achieve the above objects, the present inventors have found that, it was possible to achieve stabilization of minocycline in the oleaginous base, even without the use of stabilizers such as magnesium compounds or aluminium compounds, but with the use of an oleaginous base such as a gelated hydrocarbon in place of the conventionally used polyhydric alcohol. The present invention was completed based on these findings.

Thus, according to the present invention, there is provided a pharmaceutical composition for topical administration comprising minocycline or a physiologically acceptable salt thereof in an oleaginous base.

Preferably, the oleaginous base is a gelated hydrocarbon. More preferably, the gelated hydrocarbon is plastibase.

The pharmaceutical composition according to the present invention preferably further comprises one or more adhesive agent selected from the group consisting of cellulose, cellulose derivatives, water-soluble high molecular compounds and water-soluble starch.

The pharmaceutical composition according to the present invention preferably further comprises a disintegrant.

According to a preferred embodiment of the present invention, there is provided a pharmaceutical composition comprising:

(a) 0.01–15% by weight of minocycline or a physiologically acceptable salt thereof;
(b) 20–97% by weight of an oleaginous base;
(c) 1–60% by weight of an adhesive agent; and
(d) 1–20% by weight of a disintegrant According to a more preferred embodiment of the present invention, there is provided a pharmaceutical composition comprising:

(a) 0.01–15% by weight of minocycline hydrochloride;
(b) 20–97% by weight of a gelated hydrocarbon;
(c) 1–60% by weight of hydroxypropylmethylcellulose, alpha-converted starch, carboxyvinyl polymer or methylcellulose; and,
(d) 1–20% by weight of a sucrose fatty acid ester.

The pharmaceutical composition of the present invention is preferably used in dental treatment and/or prevention, more preferably in treatment and/or prevention of periodontal diseases.

According to another aspect of the present invention, there is provided an oleaginous base which is used as a stabilizer of minocycline or a physiologically acceptable salt thereof.

DETAILED DESCRIPTION OF THE INVENTION

The pharmaceutical composition of the present invention is characterized in that it comprises minocycline or a physiologically acceptable salt thereof in an oleaginous base. The pharmaceutical composition of the present invention can be generally prepared as a pharmaceutical composition for topical administration to the oral cavity or periodontia, and preferably as a pharmaceutical composition for dental use.

The pharmaceutical composition according to the present invention is preferably provided such that it is suitable for topical administration to the oral cavity or periodontia, for example as a composition in a viscous liquid or paste form. The pharmaceutical composition according to the present invention is useful in the treatment and/or prevention of oral cavity disease or disease in the dental area, for example, periodontal diseases such as periodontitis, periodontal disease, alveolar pyorrhea and the like. Moreover, the use of the pharmaceutical composition according to the present invention is not limited to the above embodiments and is able to be used as an external pharmaceutical composition on the skin or mucosa.

The type of a physiologically acceptable salt of minocycline is not particularly limited. For example, mineral acid salts such as chloride, sulfate or acetate or organic acid salts such as methanesulfonate can be used. Minocycline or a physiologically acceptable salt thereof may be a hydrate or solvate. A solvent which forms the solvate is not particularly limited so long as it is physiologically acceptable, and for example, solvates of ethanol and the like may be used. It is preferred that hydrochloride is used as a salt of minocycline. The content of minocycline or a physiologically acceptable salt thereof contained in the pharmaceutical composition of the present invention is generally about 0.01–15% by weight, preferably about 0.1–5% by weight (as the converted amount to free minocycline) relative to the weight of the composition.

The type of oleaginous base used in the pharmaceutical composition of the present invention is not particularly limited if it is one that is generally used in the pharmaceutical field. For example, gelated hydrocarbon, Vaseline, squalane, isostearic acid, yellow beeswax, liquid paraffin, mid-chain fatty acid triglyceride, cottonseed oil and the like can be used alone or in combination of two or more of them. Preferably, a gelated hydrocarbon may be used. Plastibase (Bristol Myers Squibb), Poloid (Maruishi Pharmaceutical) or the like can be used as the gelated hydrocarbon.

The content of the oleaginous base contained in the pharmaceutical composition of the present invention is generally 20–97% by weight, preferably 60–97% by weight, and more preferably 70–90% by weight relative to the weight of the composition.

In the pharmaceutical composition of the present invention, one or more substances selected from the group consisting of cellulose, cellulose derivatives, and water-soluble high molecular compounds may be formulated as an adhesive agent. As cellulose, crystalline cellulose can be used. Examples of cellulose derivatives that can be used include sodium carboxymethylcellulose, cellulose acetate phtalate, hydroxyethylcellulose, hydroxypropylmethylcellulose and the like. Among these, hydroxypropylmethylcellulose is preferred. Examples of water-soluble high molecular compounds include polyethylene glycol (Macrogol, etc.), polyvinyl alcohol, polyvinyl pyrolidon, Carragheenan, locust bean gum, arabia gum, xanthan gum, tragant gum, starch, etc.

The content of adhesive agent contained in the pharmaceutical composition of the present invention is generally about 1–60% by weight, preferably about 1–40% by weight, and more preferably about 5–20% by weight relative to the weight of the composition.

Further, in the pharmaceutical composition of the present invention, a disintegrant may be formulated. The disintegrant that can be used are not particularly limited so long as it is one generally used in the pharmaceutical field. Examples of the disintegrant include sucrose fatty acid ester, glycerine fatty acid ester, sodium carboxymethylcellulose, lactose, sodium bicarbonate and the like. Sucrose fatty acid ester can preferably be used. Examples of a sucrose fatty acid ester that can be used include sucrose stearate, sucrose palmitate, sucrose myristate, sucrose oleate, sucrose laureate, sucrose behenate, sucrose erucate, sucrose esters of mixed acid (oleic acid, palmitic and stearic acid) and the like.

The content of the disintegrant contained in the pharmaceutical composition of the present invention is generally about 1–20% by weight, preferably about 1–10% by weight relative to the weight of the composition.

Further, magnesium compounds (for example, the compounds described in Japanese Patent Publication No. 1-12728 and Japanese Patent Publication No. 2-34325) and/or aluminium compounds (for example, the compounds described in Japanese Patent Application Laid-Open No. 11-286448) may be formulated in the pharmaceutical composition of the present invention.

The pharmaceutical composition of the present invention can be prepared according to conventional methods, and the method for preparation is not particularly limited. For example, the pharmaceutical composition of the present invention can easily be prepared by adding minocycline or a physiologically acceptable salt thereof, an oleaginous base such as gelated hydrocarbon, a disintegrant and an adhesive agent to a vessel in given amounts, and blending them as described in the Examples below.

Further, when manufacturing the pharmaceutical composition of the present invention, additives for drug formulation available for those skilled in the art may be used appropriately. For example, a buffering agent, pH adjuster, surfactant, plasticizer, binder, dispersant, preservative and/or colorant, etc., may be formulated in the pharmaceutical composition of the present invention. The content of these additives for drug manufacture can be appropriately selected by those skilled in the art such that it is suitable for pharmaceutical compositions for oral cavity use, dental use, or external use for applying to the skin or mucosa. The pharmaceutical composition of the present invention can be prepared at a suitable elevated temperature where necessary, but in order to increase the stability of minocycline, it is preferred to prepare the pharmaceutical composition in a non-aqueous system.

The pharmaceutical composition of the present invention prepared as described above, can be administered to a patient by directly applying it to the affected area (for example, to the periodontal disease area), and is preferably administered topically to the periodontal pocket. The amount to be applied can be appropriately selected depending on the size of the affected area, extent of the disease, etc. For example, about 10–100 mg of the pharmaceutical composition of the present invention can be administered per tooth. Further, duration and number of administrations can be selected as appropriate.

The content of Japanese Patent Application No. 2000-150937, on which the present application claims a priority, is incorporated herein by reference.

The present invention will be further explained by examples below. However, these examples are not intended to limit the scope of the present invention.

EXAMPLES

Example 1

2 g (titer) of minocycline hydrochloride, 73 g of gelated hydrocarbon (Plastibase; Bristol Myers Squibb), 20 g of hydroxypropylmethylcellulose and 5 g of sodium carboxymethylcellulose were placed in a kneader and kneaded for 1 hour to produce 100 g of the pharmaceutical composition of the present invention.

Example 2

2 g (titer) of minocycline hydrochloride, 68 g of gelated hydrocarbon (Plastibase; Bristol Myers Squibb), 10 g of sucrose fatty acid ester, and 20 g of hydroxypropylmethylcellulose were placed in a kneader and kneaded for 1 hour to produce 100 g of the pharmaceutical composition of the present invention.

Example 3

2 g of minocycline hydrochloride, 79 g of gelated hydrocarbon (Plastibase; Bristol Myers Squibb) and 5 g of sucrose fatty acid ester, and 14 g of hydroxypropylmethylcellulose were placed in a kneader and kneaded for 1 hour to produce the pharmaceutical composition of the present invention.

Test Example 1

The pharmaceutical compositions of the present invention prepared in Examples 1 to 3, were stored for 6 months under the condition of 30° C. and 70% relative humidity. The titer of post-storage minocycline was measured in accordance with the cylinder plate method described in *Japanese Antibiotic Standard Commentary* (1993). The sample liquid was prepared as follows. A mass corresponding to approximately 10 mg (titer) was weighed precisely, and 10 ml of dimethyl formamide was added thereto to dissolve it. Then, 0.1M phosphate buffer (pH4.5) was added to bring the solution to exactly 100 ml, thereby preparing a solution having a concentration of about 0.1 mg (titer)/ml. An appropriate amount of this liquid was weighed out precisely and a sample solution of a prescribed concentration was prepared by precise dilution with 0.1M phosphate buffer (pH4.5).

As a result of this measurement, no significant reduction in titer of minocycline hidrochloride could be recognized in respect of any of the pharmaceutical compositions of Examples 1 to 3

Example 4

Macrogol 1500 (30 g) and Macrogol 400 (20 g) were placed in a beaker and made uniform by heating/agitation with a hot stirrer. 44 g of this mixture, and 2 g (titer) of minocycline hydrochloride, 30 g of gelated hydrocarbon, 13.9 g of hydroxypropylmethylcellulose, 10 g of calcium chloride, and 0.1 g zinc sulfate were placed in a kneader and kneaded for 1 hour to produce 100 g of the pharmaceutical composition of the present invention.

Example 5

86 g of white Vaseline, 3 g of cholesterol, 3 g of stearyl alcohol, 8 g of white beeswax were placed in a beaker and made uniform by heating/agitation with a hot stirrer. 93 g of this mixture, 2 g (titer) of minocycline hydrochloride, 5 g carboxyvinyl polymer were placed in a kneader and kneaded for 1 hour to produce 100 g of the pharmaceutical composition of the present invention.

Comparative Example 1

2 g (titer) of minocycline hydrochloride, 95 g of concentrated glycerin, and 3 g of sodium carboxymethylcellulose were placed in a kneader and kneaded for 1 hour to produce 100 g of the pharmaceutical composition of the present invention.

Test Example 2

A syringe was filled with the pharmaceutical composition prepared in Examples 4 and 5, and Comparative Example 1, tightly sealed, and stored for 15 hours at 50° C. As a result of comparing each of the post-storage compositions of Examples 4 and 5, and Comparative example 1, a change in characteristics was recognized in the composition of the Comparative Example, but no change was recognized in those of Examples 4 and 5.

Industrially Applicable Field

The minocycline-containing pharmaceutical composition of the present invention is stable, and is particularly useful in the treatment and/or prevention of dental diseases such as periodontitis, periodontal disease, or alveolar pyorrhea.

What is claimed is:

1. A pharmaceutical composition comprising:
   0.01–15% by weight of minocycline or a physiologically acceptable salt thereof;
   20–97% % by weight of an oleaginous base;
   1–60% by weight of an adhesive agent; and,
   1–20% by weight of a sucrose fatty acid ester.

2. The pharmaceutical composition according to claim 1 wherein the oleaginous base is a gelated hydrocarbon.

3. The pharmaceutical composition according to claim 1 further comprising at least one adhesive agent selected from the group consisting of cellulose, cellulose derivatives, water-soluble high molecular compounds, and water-soluble starch.

4. The pharmaceutical composition according to claim 1, which comprises:
   0.01–15% by weight of minocycline hydrochloride;
   20–97% by weight of a gelated hydrocarbon;
   1–60% by weight of a hydroxypropylmethylcellulose, alpha-converted starch, carboxyvinyl polymer or methylcellulose; and
   1–20% by weight of a sucrose fatty acid ester.

5. A method for at least one of treatment and prevention of dental diseases comprising topically administering to a patient a pharmaceutical composition comprising minocycline or a physiologically acceptable salt thereof, an oleaginous base and a sucrose fatty acid ester.

6. The method according to claim 5 wherein the at least one of treatment and prevention of dental diseases comprises at least one of treatment and prevention of a periodontal disease.

7. A method of stabilizing a minocycline or a physiologically acceptable salt thereof comprising combining the minocycline or a physiologically acceptable salt thereof with an oleaginous base and a sucrose fatty acid ester.

8. The method according to claim 5 wherein the oleaginous base is a gelated hydrocarbon.

9. The method according to claim 5, wherein the pharmaceutical composition comprises:

0.01–15% by weight of minocycline or a physiologically acceptable salt thereof;

20–97% by weight of an oleaginous base;

1–60% by weight of an adhesive agent; and,

1–20% by weight of a sucrose fatty acid ester.

10. The method according to claim 9, which comprises:

0.01–15% by weight of minocycline hydrochloride;

20–97% by weight of a gelated hydrocarbon;

1–60% by weight of a hydroxypropylmethylcellulose, alpha-converted starch, carboxyvinyl polymer or methylcellulose; and, 1–20% by weight of a sucrose fatty acid ester.

11. The method according to claim 6 wherein the oleaginous base is a gelated hydrocarbon.

12. The method according to claim 6, wherein the pharmaceutical composition comprises:

0.01–15% by weight of minocycline or a physiologically acceptable salt thereof;

20–97% by weight of an oleaginous base;

1–60% by weight of an adhesive agent; and,

1–20% by weight of a sucrose fatty acid ester.

13. The method according to claim 12, wherein comprises:

0.01–15% by weight of minocycline hydrochloride;

20–97% by weight of a gelated hydrocarbon;

1–60% by weight of a hydroxypropylmethylcellulose, alpha-converted starch, carboxyvinyl polymer or methylcellulose; and, 1–20% by weight of a sucrose fatty acid ester.

14. The method according to claim 7 wherein the oleaginous base is a gelated hydrocarbon.

* * * * *

UNITED STATES PATENT AND TRADEMARK OFFICE
CERTIFICATE OF CORRECTION

PATENT NO. : 6,566,350 B2
DATED : May 20, 2003
INVENTOR(S) : Kazuhiro Ono et al.

It is certified that error appears in the above-identified patent and that said Letters Patent is hereby corrected as shown below:

Column 6,
Line 36, delete "%" (second occurrence).

Column 8,
Line 10, "wherein" should be -- which --.

Signed and Sealed this

Twenty-seventh Day of January, 2004

JON W. DUDAS
*Acting Director of the United States Patent and Trademark Office*